United States Patent
Goad (10) Patent No.: US 9,442,103 B1
(45) Date of Patent: Sep. 13, 2016

(54) ANTI-CIRCUMVENTION APPARATUS AND METHODS FOR USE IN SOBRIETY TESTING SYSTEMS

(71) Applicant: 1A Smart Start, Inc., Irving, TX (US)

(72) Inventor: Richard Goad, Flower Mound, TX (US)

(73) Assignee: 1A Smart Start LLC, Grapevine, TX (US)

( * ) Notice: Subject to any disclaimer, the term of this patent is extended or adjusted under 35 U.S.C. 154(b) by 224 days.

(21) Appl. No.: 13/932,804

(22) Filed: Jul. 1, 2013

Related U.S. Application Data (60) Provisional application No. 61/781,748, filed on Mar. 14, 2013.

(51) Int. Cl.
*G01N 1/22* (2006.01)
*G01N 33/497* (2006.01)

(52) U.S. Cl.
CPC .................. *G01N 33/4972* (2013.01)

(58) Field of Classification Search
CPC ........... G01N 33/497; G01N 33/4972; G01N 21/3504; A61B 5/097; A61B 5/082
USPC ........................................... 73/23.3
See application file for complete search history.

(56) References Cited

U.S. PATENT DOCUMENTS

| | | | |
|---|---|---|---|
| 4,678,057 A | 7/1987 | Elfman et al. | |
| 5,247,185 A * | 9/1993 | Herrera | G01J 3/108 219/497 |
| 6,167,746 B1 | 1/2001 | Gammenthaler | |
| 6,792,793 B2 | 9/2004 | Mendoza | |
| 8,686,864 B2 * | 4/2014 | Hannon | H04K 3/415 180/271 |
| 8,957,771 B2 * | 2/2015 | Arringdale | B60K 28/063 180/272 |
| 2001/0037070 A1 * | 11/2001 | Cranley | A61B 5/00 600/532 |
| 2006/0237253 A1 * | 10/2006 | Mobley | B60K 28/063 180/272 |
| 2012/0055726 A1 * | 3/2012 | Hannon | B60R 25/00 180/272 |
| 2012/0228047 A1 | 9/2012 | White et al. | |

OTHER PUBLICATIONS

Written Opinion of the International Search Authority mailed Aug. 11, 2014 for PCT/US2014/024631.
International Search Report mailed Aug. 11, 2014 for PCT/US2014/024631.

* cited by examiner

*Primary Examiner* — Eric S McCall
*Assistant Examiner* — Mohammed E Keramet-Amircola
(74) *Attorney, Agent, or Firm* — Thompson & Knight LLP; James J. Murphy (57) ABSTRACT

A method for preventing circumvention of a intoxication test includes defining a detection time envelope with a first sensor activated in response to the presence of a human test subject proximate the first sensor and sensing with a second sensor for a change from an ambient condition caused by the presence of the human test subject proximate the second sensor. The intoxication test is validated when a change from the ambient condition is detected by the second sensor during the time envelope defined by the first sensor.

16 Claims, 11 Drawing Sheets

ANTI-CIRCUMVENTION APPARATUS AND METHODS FOR USE IN SOBRIETY TESTING SYSTEMS

CROSS-REFERENCE TO RELATED APPLICATION

The present application claims the benefit of U.S. Provisional Patent Application Ser. No. 61/781,748, filed Mar. 14, 2013, which is incorporated herein by reference for all purposes.

FIELD OF INVENTION

The present invention relates in general to sobriety testing techniques, and in particular to anti-circumvention apparatus and methods for use in sobriety testing systems.

BACKGROUND OF INVENTION

Sobriety testing, which includes testing for both alcohol and illegal drugs, has taken a prominent role in ensuring a safe and efficient society. For example, ignition interlocks on vehicles have proven their worth in preventing intoxicated drivers from entering the roadways and causing serious, including fatal, accidents. Sobriety testing has also allowed authorities, such as courts and law enforcement agencies, to monitor compliance with the court-ordered restrictions imposed on persons having committed an alcohol or drug related offense. Among other things, with the availability of reliable sobriety testing systems, such offenders can continue travel to work, school, or rehabilitation and thus contribute to society, rather than be a burden.

Attempts to circumvent these sobriety testing systems is significant problem. For example, an intoxicated driver might try to circumvent a breathalyzer-based vehicle sobriety interlock system by introducing air from an air compressor, compressed air canister, balloon, or other source of intoxicant-free air. And while a number of anti-circumvention techniques suitable for use in sobriety testing systems are known in the art, these techniques are subject to a number of significant limitations. For example, some known anti-circumvention techniques used with breathalyzer-based systems require that the person being tested manipulate the breath air flow into the test apparatus. In the blow-hum technique, the user starts with a normal blow of air, then switches to a blow of air combined with a hum. In the blow-suck technique, the user starts with a normal blow then quickly reverses to a suck or inhale. In the blow-blow technique, the user starts with a normal blow then changes to a harder blow or softer blow.

These air manipulation techniques are subject to some serious disadvantages. Among other things, they are difficult for the human test subject to master and require consistency and patience for even sober users to pass each time. Moreover, the blow-suck technique can be unhygienic.

SUMMARY OF INVENTION

According to one representative embodiment of the principles of the present invention, a method is disclosed for preventing circumvention of an intoxication test, which includes defining a detection time envelope with a first sensor activated in response to the presence of a human test subject proximate the first sensor. A second sensor senses for a change from an ambient condition caused by the presence of the human test subject proximate the second sensor. The intoxication test is validated when a change from the ambient condition is detected by the second sensor during the time envelope defined by the first sensor.

According to a particular embodiment of the inventive principles, the first sensor is a capacitive proximity sensor, which detects a change in capacitance caused by the presence of the human test subject in a surrounding detection field. In intoxication testing systems employing breath tests, the first sensor may also be a pressure sensor, which measures breath air pressure provided by the human test subject. In some embodiments, both a capacitive proximity sensor and a pressure sensor are used to define the detection time envelope.

In particular embodiments of the principles of the present invention, the second sensor is either an infrared thermometer measuring a temperature of the human test subject, a humidity sensor, a breath temperature sensor, or a combination of two or more of these sensors.

Embodiments of the present principles advantageously address the problems associated with the conventional breath manipulation techniques used to provide anti-circumvention protection in intoxication testing systems. In the case of breath testing systems, the need to master the blow-hum, blow-suck, and/or blow-blow techniques is substantially reduced or eliminated. Moreover, the principles of the present invention are applicable to a wide range of intoxication testing devices and systems with the potential for circumvention, including breath testing devices for vehicle interlock systems, stand alone breath testing devices, and similar devices and systems for alcohol and controlled substances.

BRIEF DESCRIPTION OF DRAWINGS

For a more complete understanding of the present invention, and the advantages thereof, reference is now made to the following descriptions taken in conjunction with the accompanying drawings, in which.

DETAILED DESCRIPTION OF THE INVENTION

The principles of the present invention and their advantages are best understood by referring to the illustrated embodiment depicted in FIGS. 1-5 of the drawings, in which like numbers designate like parts. For discussion purposes, these principles will be described in conjunction with an alcohol breath testing system operating within an vehicle ignition interlock system. It should be recognized, however, that the anti-circumvention systems and methods described below are equally applicable to other types of sobriety testing systems, including stand-alone sobriety testing systems and those designed to test for other types of intoxicants and controlled substances (e.g., marijuana).

Figure 1A:
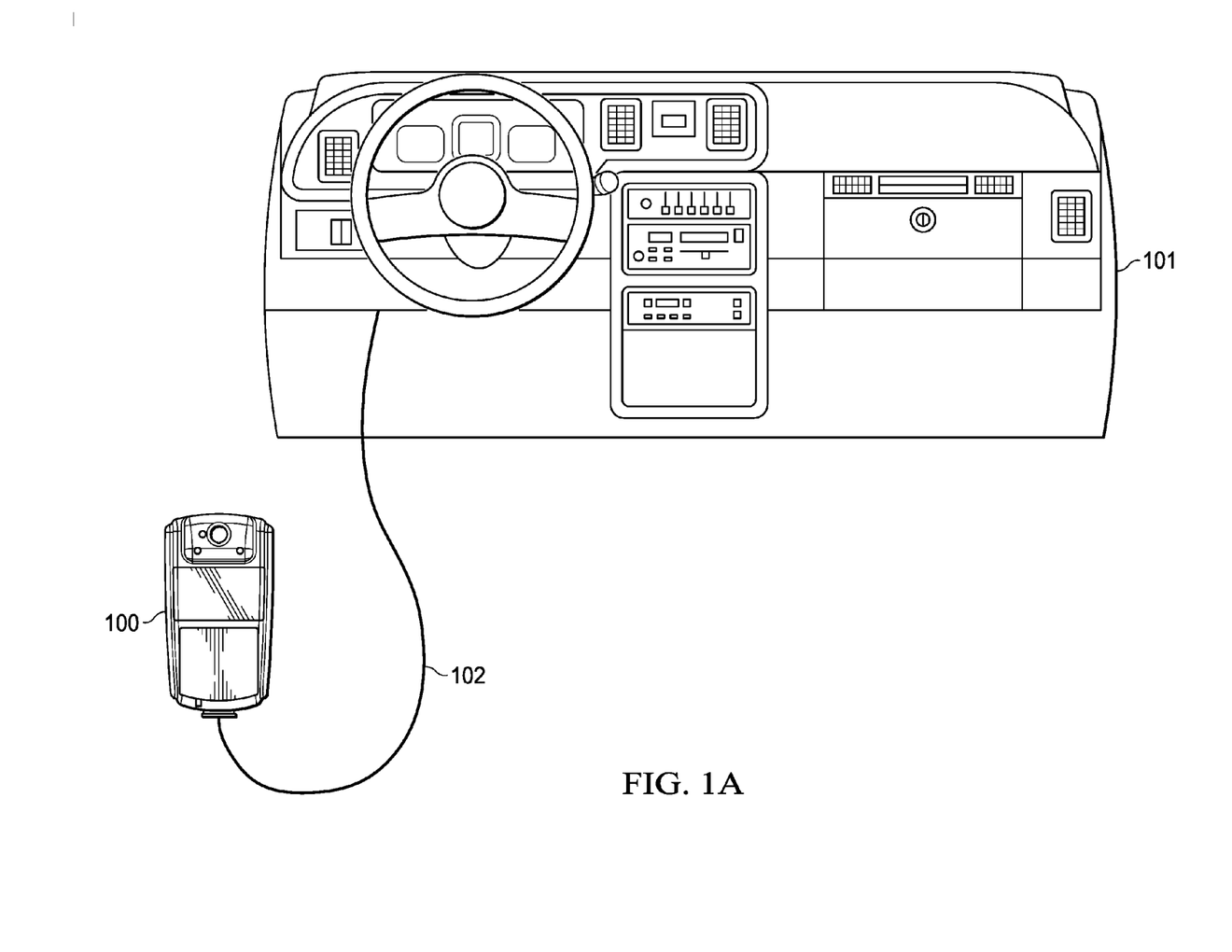
FIG. 1A is a diagram of a portion of an interior of a vehicle including a sobriety interlock system suitable for demonstrating one possible application of the principles of the present invention.

FIG. 1A is a diagram showing a portion of the interior of a motor vehicle in the area of the dashboard. A handheld breath alcohol testing unit 100 is connected to electronic circuitry behind vehicle dashboard 101 (see FIG. 1B) through a cable 102. Generally, a person attempting to start the vehicle must provide a breath sample to handheld unit 102, which tests for deep-lung breath alcohol content, deep-lung alcohol content being directly proportional to blood alcohol concentration and thus intoxication level. If the person being tested passes the breath alcohol test, the interlock system allows the vehicle to start. On a test failure, the interlock system disables the vehicle ignition system and the vehicle is rendered inoperable.

Figure 1B:
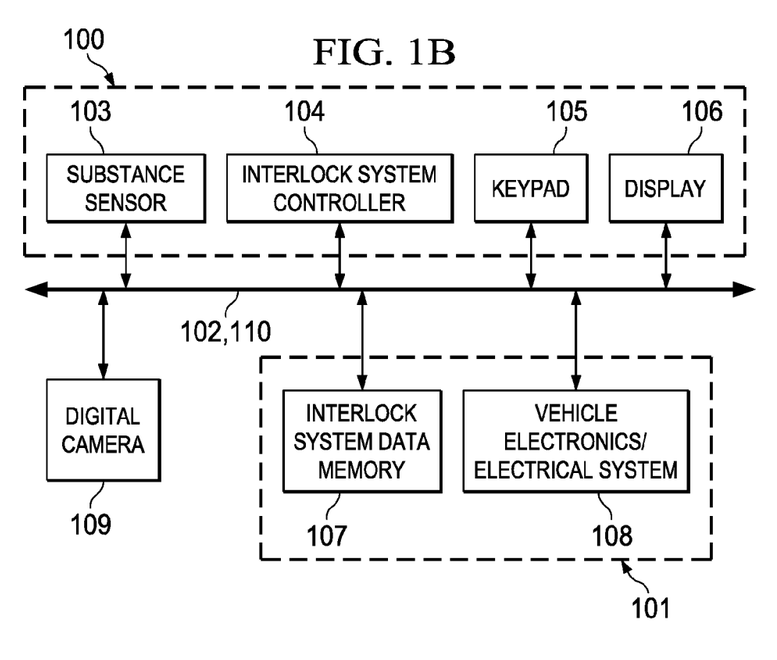
FIG. 1B is a high level functional block diagram of the exemplary sobriety interlock system utilized in the application shown in FIG. 1A.

FIG. 1B is a high level functional block diagram of the overall interlock system. Handheld unit 100, which is discussed in detail below, includes a substance sensor 103, which in the illustrated embodiment is a fuel cell alcohol sensor, an interlock system controller 104, a keypad 105 for data entry, and a display 106.

Handheld unit 100 electrically communicates through cable 102 with electronics behind dashboard 101, including interlock system memory 107 and vehicle electronics/electrical system 108. Interlock system data memory 107, which is preferably solid state memory, such as Flash memory, stores the results of tests performed by handheld unit 100 for periodic retrieval and review by authorities monitoring the driver for compliance with any conditions or restrictions imposed on the driver. While interlock system controller 104 is located within handheld unit 100 in the embodiment shown in FIG. 1B, it may be located along with interlock data memory 107 behind dashboard 101 in alternate embodiments.

Vehicle electronics/electrical system 108 controls the operation of the vehicle in response to the outcome of a given test. As known in the art, the ignition system of a vehicle can be controlled in any one of a number of ways, including enabling or disabling relays providing power to the starter motor or sending enable or disable commands to one or more on-board computers. Vehicle electronics/electrical system 108 may also be used to generate visible or audible warnings in the event of a failed test, for example, causing the horn to sound or the headlights to flash.

A digital camera 109 or similar imaging device is also preferably provided to allow for positive identification of the person taking the breath test through handheld unit 100. The images taken by digital camera 109 are preferably stored in interlock system data memory 107 for retrieval and review by the monitoring authorities. Advantageously, digital camera 109 reduces the possibility of a restricted or intoxicated driver of circumventing the interlock system by having a substitute person providing the breath sample to handheld unit 100.

In one particular embodiment, handheld unit 100, interlock system data memory 107, vehicle electronics/electrical system 108 communicate, either in whole or in part, with the OBD-II diagnostic system standard on most motor vehicles. The OBD-II system provides an efficient mechanism by which monitoring authorities can access the data stored within interlock system data memory 107 through a standard OBD-II port and associated test equipment. In addition, the OBD-II also allows for vehicle operating data to be recorded and stored within interlock system data memory 107 for correlation with the results of sobriety testing performed through handheld unit 100.

The OBD-II diagnostic system also provides a communications path for transmission of command and control signals from interlock system controller 104 to vehicle electronics/electrical system 108. These command and control signals can be used by interlock system controller 104 to disable the vehicle in response to a failed intoxication test.

Figure 2:
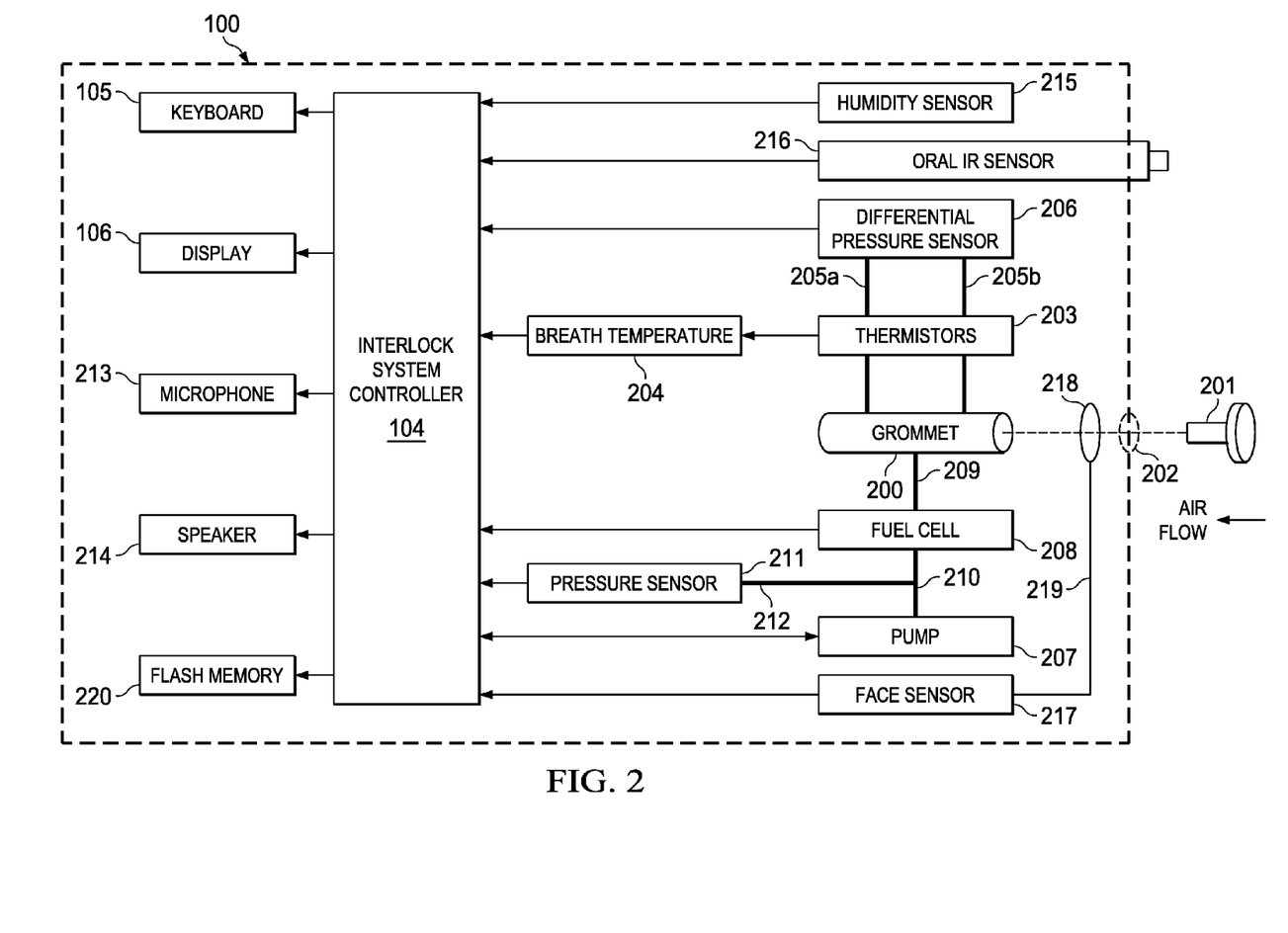
FIG. 2 is a more detailed functional block diagram showing the primary subsystems of the handheld unit shown in FIG. 1B.

FIG. 2 is a more detailed functional block diagram of the primary subsystems within handheld unit 100 in a preferred embodiment of the principles of the present invention. In this embodiment, interlock system controller 104 is a Renesas RSF3650KDFB processor operating in conjunction with firmware stored in Flash memory 220. For clarity, interface devices, such as the analog to digital converters (ADCs) interfacing the various blocks with controller 104, and auxiliary subsystems, such has the fuel cell and grommet heaters, are not shown in FIG. 2.

Figure 4A:
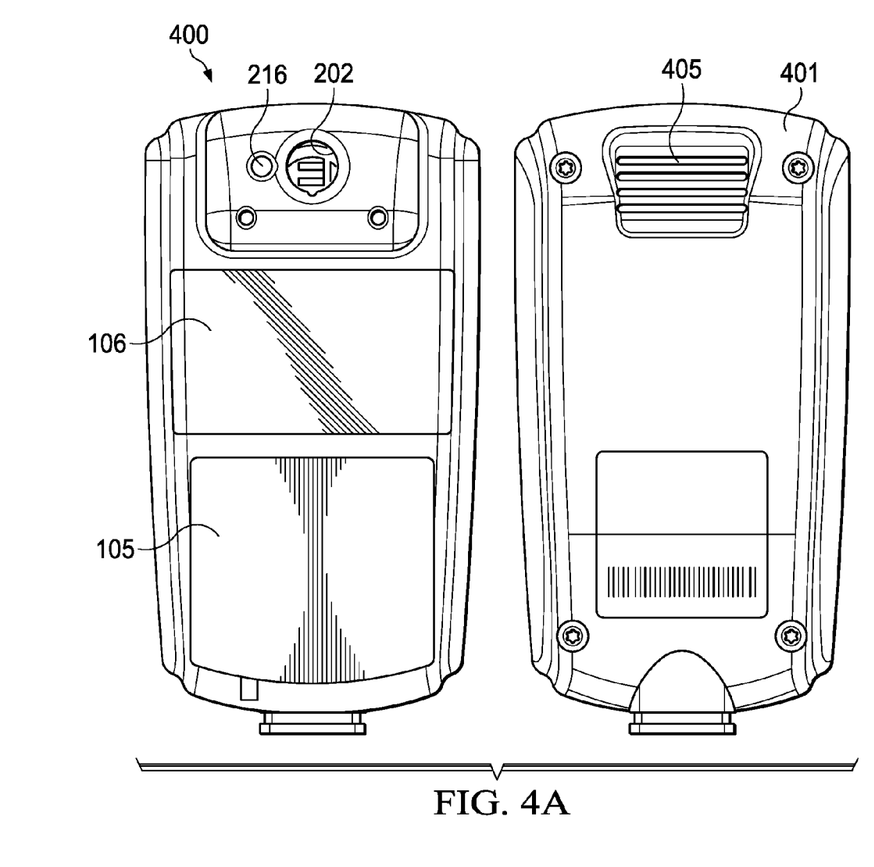
FIG. 4A is a plan view diagram showing the outer surfaces front and back panels forming the case of the handheld unit shown in FIG. 1A.

A cylindrical grommet 200 receives a disposable mouthpiece 201 through an aperture 202 through the front panel of the case of handheld unit 100 (see FIG. 4A). Air introduced by a user (i.e., the human test subject) through mouthpiece 201 generally passes through cylindrical grommet 200 and passes out an aperture through the unit rear panel.

As air flow passes through grommet 200, a set of at least one thermistor 203 and associated breath temperature measurement circuitry 204 measure breath temperature. As discussed further below, breath temperature is one parameter useful for detecting attempts to circumvent an alcohol breath test.

A pair of tubes 205a-205b tap the airflow through grommet 200 to a differential pressure sensor 206, which measures breath pressure and breath air flow rate. As known in the art, in order for an alcohol breath test to be valid, the user must provide sufficient air pressure for a sufficiently long period of time to ensure that a deep-lung air is received by the alcohol sensor. If neither of these two conditions is met, interlock system controller 104 aborts the test and the breath test functional routine is reset. One device suitable for use as differential pressure sensor 206 in the embodiment of FIG. 2 is a Sensormatic 35AL-L50D-3210 differential pressure transducer.

Once interlock system controller 104 determines that deep-lung air is being received, a pump 207 is activated to draw a sample of the air flowing through grommet 200 into a fuel cell 208. In the illustrated embodiment, the air sample is drawn through tubes 209 and 210. A pressure sensor 211 monitors the air pressure being provided by pump 207 through a tube 212. One suitable fuel cell 208 is a Dart Sensors LTD 2-MS3 fuel cell operating in conjunction with a pump 207 available from PAS International, although other commercially available fuel cells and pumps may be used in alternative embodiments. A suitable device for pressure sensor 211 is a Sensormatic 33AL-L50D-3210 pressure transducer.

Fuel cell 207 implements a well-known electrochemical process to determine the breath alcohol content of the deep-lung air sample. From the air sample, interlock system controller 104 calculates the corresponding blood alcohol concentration and determines whether the user has passed or failed the test, depending on the legal limits imposed by the given jurisdiction. In response to the test result, interlock system controller 104 sends commands to vehicle electronics/electrical system 108 to enable or disable the vehicle ignition system. The results of the test are also recorded within interlock system data memory 107 for access by the monitoring authorities.

The user interacts with system controller 104 through keypad 105 and display 106, which allow the user to receive prompts and initiate a test in anticipation of starting the vehicle. In addition, interlock system controller 104 may periodically require retest of the user to ensure driver sobriety after initial start of the vehicle. In alternate embodiments, a microphone 213 and speaker 214 allow for control of handheld unit 100 by voice command.

According to the principles of the present invention, multiple sensors are provided for preventing circumvention of the breath test. In addition to breath temperature circuitry 204, handheld unit 100 also includes a humidity sensor 215, an oral infrared (IR) sensor 216, and a face proximity sensor 217. In the embodiment shown in FIG. 2, face proximity sensor 217 operates in conjunction with an electrode 218 disposed on the inner surface of the front panel of the case of handheld unit 100 and at least partially surrounding aperture 202. A clip 219 provides an electrical connection between the printed circuit board on which face proximity sensor circuit 217 resides and electrode 218 (see FIG. 4E).

Figure 3A:
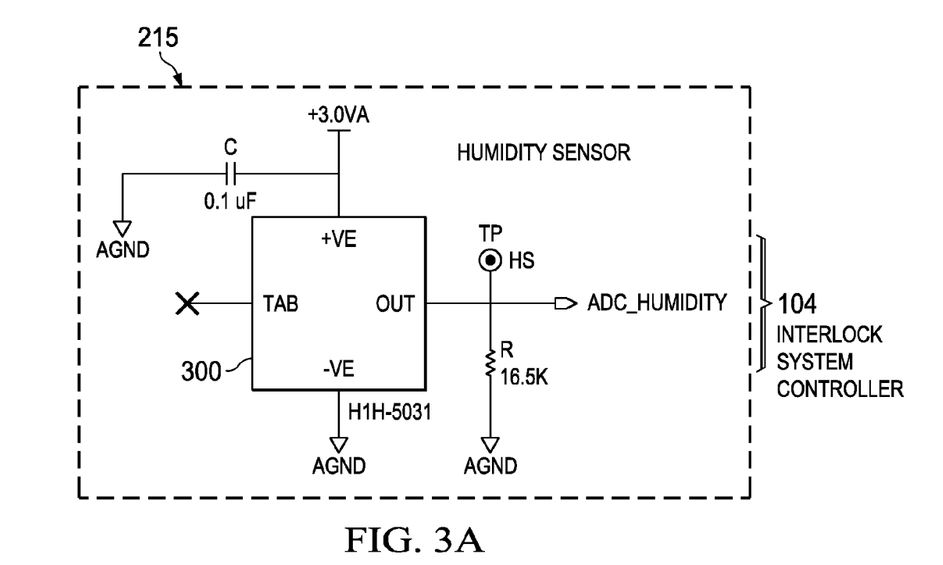
FIG. 3A is an electrical schematic diagram of the humidity sensor shown in FIG. 2.

FIG. 3A is an electrical schematic diagram of a preferred embodiment of humidity sensor 215. In the illustrated embodiment, humidity sensor 215 is based on a Honeywell HIH-5031-001 humidity sensor integrated circuit 300, which measures relative humidity using a laser trimmed, thermoset polymer capacitive sensing element with on-chip integrated signal conditioning. Humidity sensor 215 measures changes in capacitance based upon increases or decreases in ambient humidity levels. Preferably, humidity sensor 215 is protected by a screen against condensation that can produce sensor saturation.

In the idle state, humidity sensor 215 measures the relative humidity and outputs a consistent voltage level. Human breath normally contains greater than 85% humidity. Hence, when human breath is introduced in the area surrounding humidity sensor 215, the output voltage of humidity sensor 215 is expected to rise or fall from its initial reading at ambient.

In environments where the ambient relative humidity approaches that of human breath, detection of a change in relative humidity around the case of handheld unit 100 becomes more difficult. In particular, at humidity levels of 0 to 80%, the humidity sensor will respond with a detectable increase in output voltage level. However, at ambient humidity levels at or above 80%, the response curve of humidity sensor 215 flattens out, making any change due to the presence of human breath difficult or impossible to detect. In the case of high ambient humidity levels, human breath will cause the output from humidity sensor 215 to decrease. The output of humidity sensor 215 is either not used as the sole source of circumvention detection or simply discarded by interlock system processor 104 in the event that no measurable change in relative humidity over ambient is detected in the presence of human breath (i.e., the output response is flat).

Figure 3B:
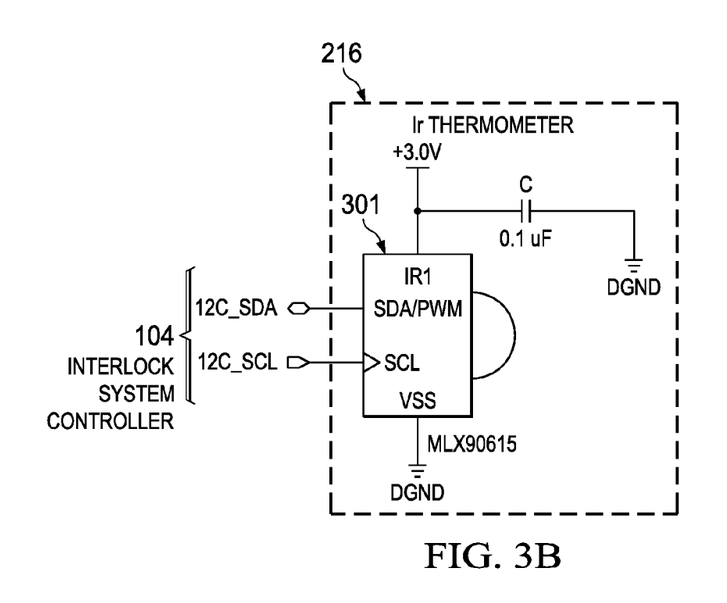
FIG. 3B is an electrical schematic diagram of the oral IR sensor shown in FIG. 2.

FIG. 3B is an electrical schematic diagram of a preferred embodiment of oral IR sensor 216, which is based on a Melixis MLX90615 infrared thermometer integrated circuit 301. Generally, an infrared thermometer reflects a beam off a target object to measure temperature and can be adjusted for the emissivity level of the intended target object.

In the preferred embodiment of handheld unit 100 shown in FIG. 2, the intended target of oral IR sensor 216 is the back of the throat of the user taking the breath test. In particular, the IR beam travels through a small relatively transparent window through the otherwise generally opaque body of mouthpiece 201. The emissivity of the opaque body of mouthpiece 201 differs from the back of the human throat. Most of the IR beam passes through the window in mouthpiece 201 to measure the temperature at the back of the user's throat; however, enough of the IR beam is reflected by the opaque mouthpiece body to provide a sufficient ambient temperature reference voltage. (For circumvention detection, an accurate body temperature measurement is not required.) The differential between the ambient temperature and the temperature at the back of the user's throat is used as an indicator of a valid test.

Figure 3C:
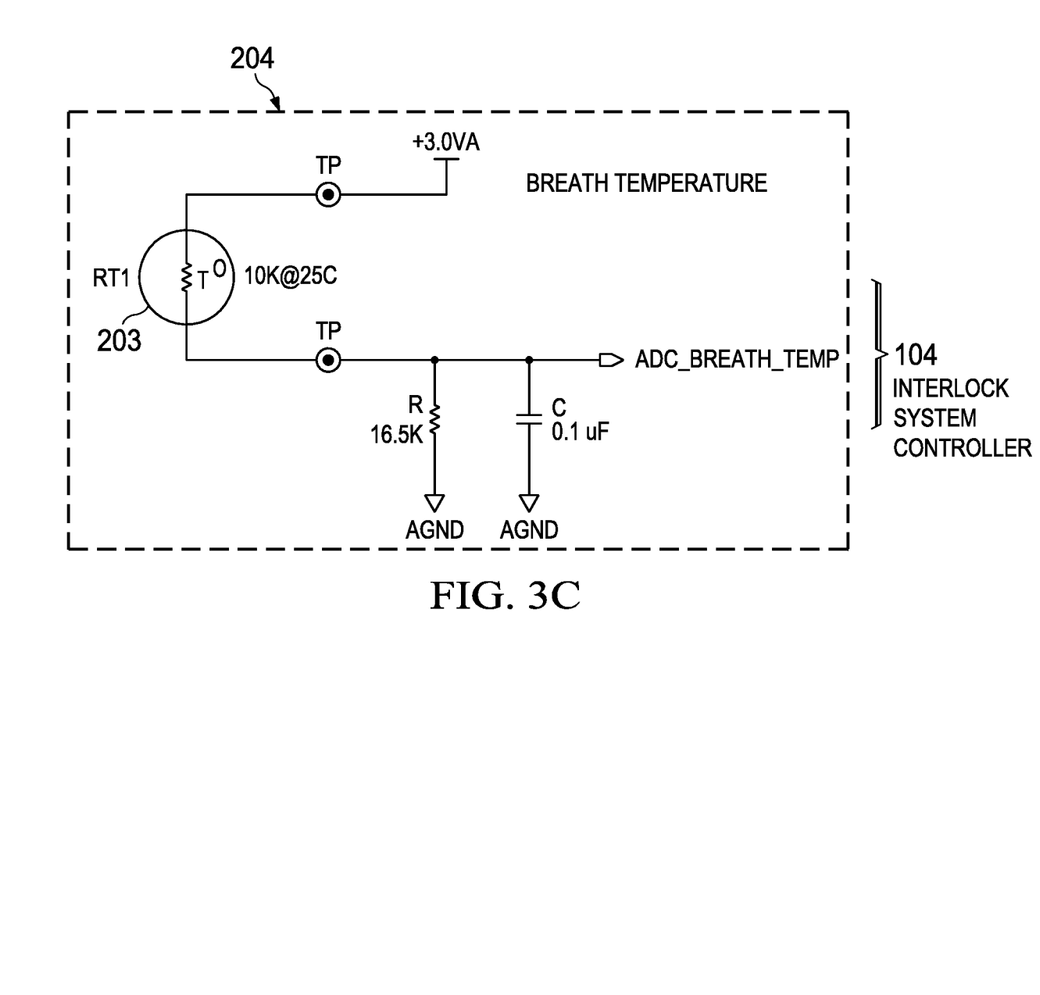
FIG. 3C is an electrical schematic diagram of the breath temperature sensor shown in FIG. 2.

FIG. 3C is an electrical schematic of breath temperature circuitry 204 and associated thermistors 203. Thermistors 203 are preferably glass encapsulated NTC thermistors that function on the principle of a proportionate resistive change versus measured temperature. As temperature increases resistance decreases, and vice versa. In other words, at lower temperatures, resistance will be high and at higher temperatures, resistance will be low. Breath temperature circuitry 204 constantly monitors the ambient temperature. As a breath sample is administered and air flows through grommet 200, the change in temperature from ambient is continuously monitored and recorded as the resistance changes.

The breath passing across the thermistors 203 will either heat or cool the sensor. In cold ambient temperatures, the breath sample will increase the measured temperature. In warmer or hot ambient temperature ranges, the breath sample will decrease in measured temperature. (In ambient conditions that are close to body temperature, or approximately 37° C., it is possible there could be no change or a very slight change that may not be discernible. In this case, interlock system control processor 104 discards the breath temperature results)

Figure 3D:
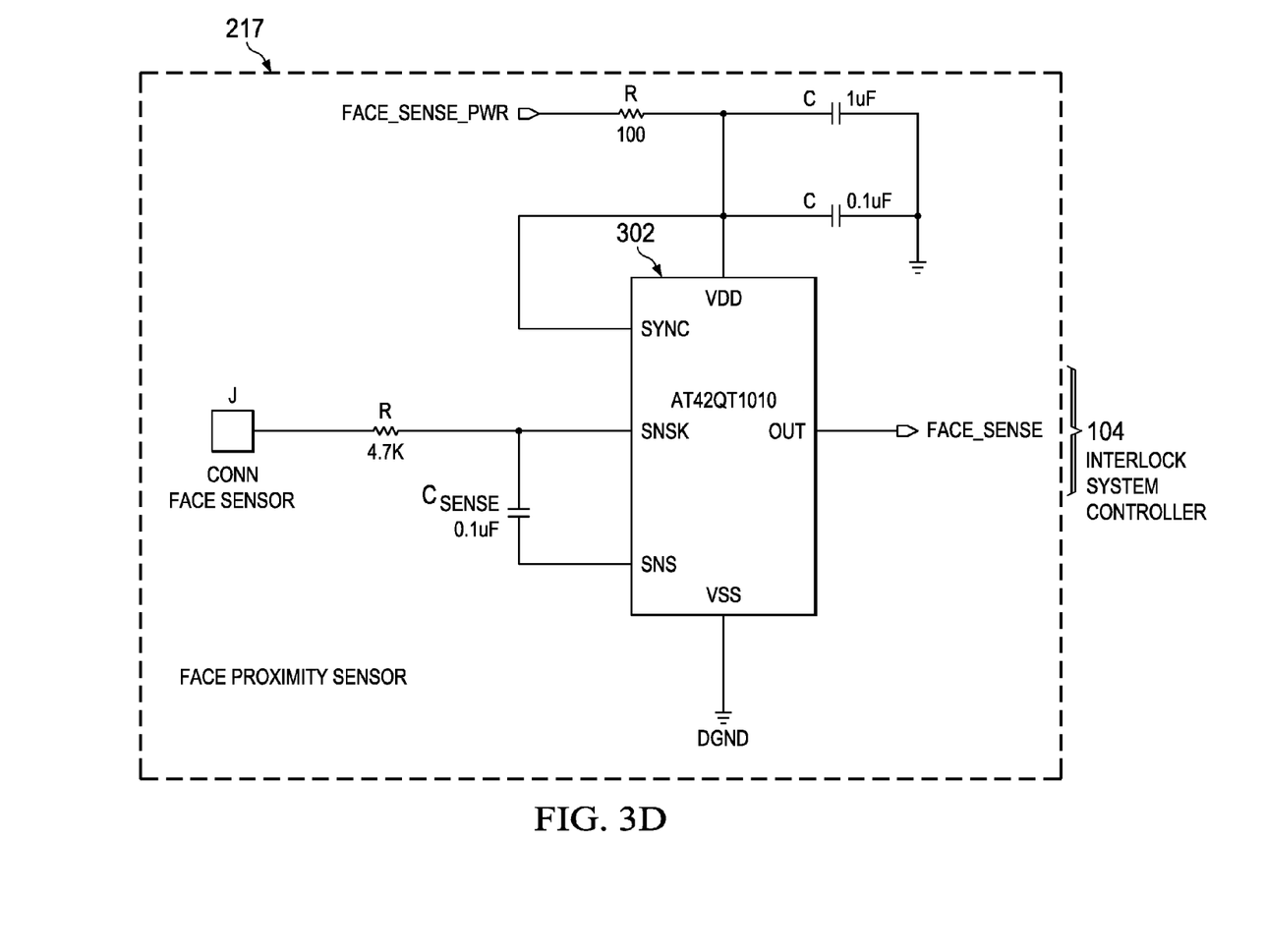
FIG. 3D is an electrical schematic diagram of the face proximity sensor shown in FIG. 2.

FIG. 3D is an electrical schematic diagram of face proximity sensor 217. In the preferred embodiment, face proximity sensor 217 is based on an Atmel AT42QT1010 capacitive touch sensor integrated circuit 302, which detects differences in capacitance when a human body approaches electrode 218 on case of handheld unit 100. Specifically, electrode 218, which is not grounded within handheld unit 100, uses the inherent capacitance of the human body within the detection field to establish a return path to ground, which is detected by face proximity sensor 217.

Advantageously, the face proximity sensor system is a non-mechanical contactless design and is not susceptible to temperature changes. However, since face proximity sensor 217 works by measuring small changes in capacitance, it can be sensitive to atmospheric changes, such as humidity. It is therefore critical to ensure that face proximity sensor 217 and associated circuitry are conformal coated.

To activate face proximity sensor 217, the user places their lips around the base of mouthpiece 201 to be within the detection field. When triggered, face proximity sensor 217 provides a digital voltage output that is equal to the power supply voltage. The output level stays high as long as the sensor is triggered. This creates an envelope that can be used in a multiple sensor anti-circumvention technique discussed below. In the preferred embodiment, a logic 0 means the sensor is not active, and a logic 1 means the sensor is active and a human face has been detected.

The sensitivity of face proximity sensor 217 can be varied using capacitor $C_{Sense}$. In an embodiment using the Atmel AT42QT1010 touch sensor integrated circuit 302, the recommended range of values for capacitor $C_{Sense}$ is 5 to 50 nF. Larger values for $C_{Sense}$ generally increase the sensitivity, although too large a value can increase noise susceptibility and false triggers. In the preferred embodiment, a 0.033 uF value for capacitor $C_{Sense}$ was found to provide a detection field in which the user only has to place their lips half way down mouthpiece 201. Alternatively, with a value of the 0.022 uF, light contact to the base of mouthpiece 201 was needed to ensure triggering the sensor.

The Atmel AT42QT1010 device can, in some cases, get stuck in the enabled position (not the disabled). If this happens, the face proximity sensor 217 will automatically reset itself and return to the disabled position. If power to the face sensor chip 302 is provided from the programmable input/output pin of interlock system processor 104, the system firmware can provide for faster reset and force recalibration.

FIG. 4A provides views of front panel 400 and back panel 401 of the preferred plastic case of handheld unit 100. Front panel 400 includes aperture 202 for receiving disposable mouthpiece 201 into grommet 200, along with display 106 and keypad 105. Back panel 401 includes an aperture 405 allowing air passing through grommet 200 to exit handheld unit 100.

Figure 4B:
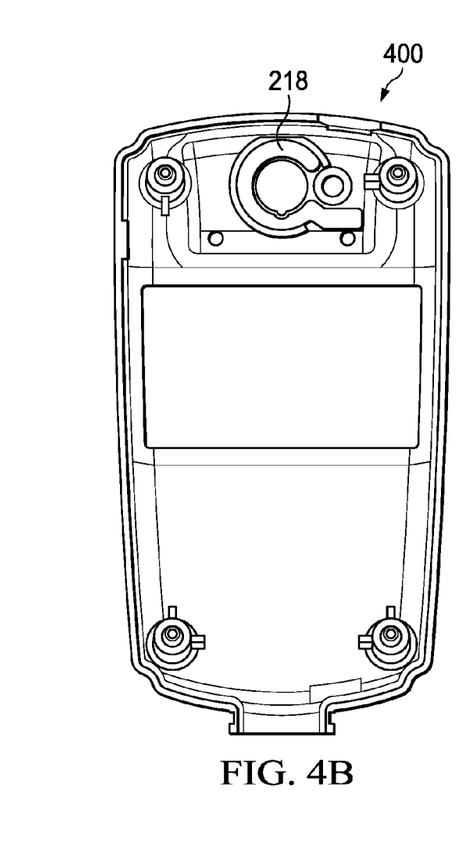
FIG. 4B is a plan view diagram showing the inner surface of front panel shown in FIG. 4A, including the face sensor electrode shown in FIG. 2.

FIG. 4B shows the inside surface of front panel 400, including proximity detection electrode 218, which extends around the periphery of aperture 202. Preferably, the surface of electrode 218 is four times the thickness of plastic front panel 400.

Figure 4C:
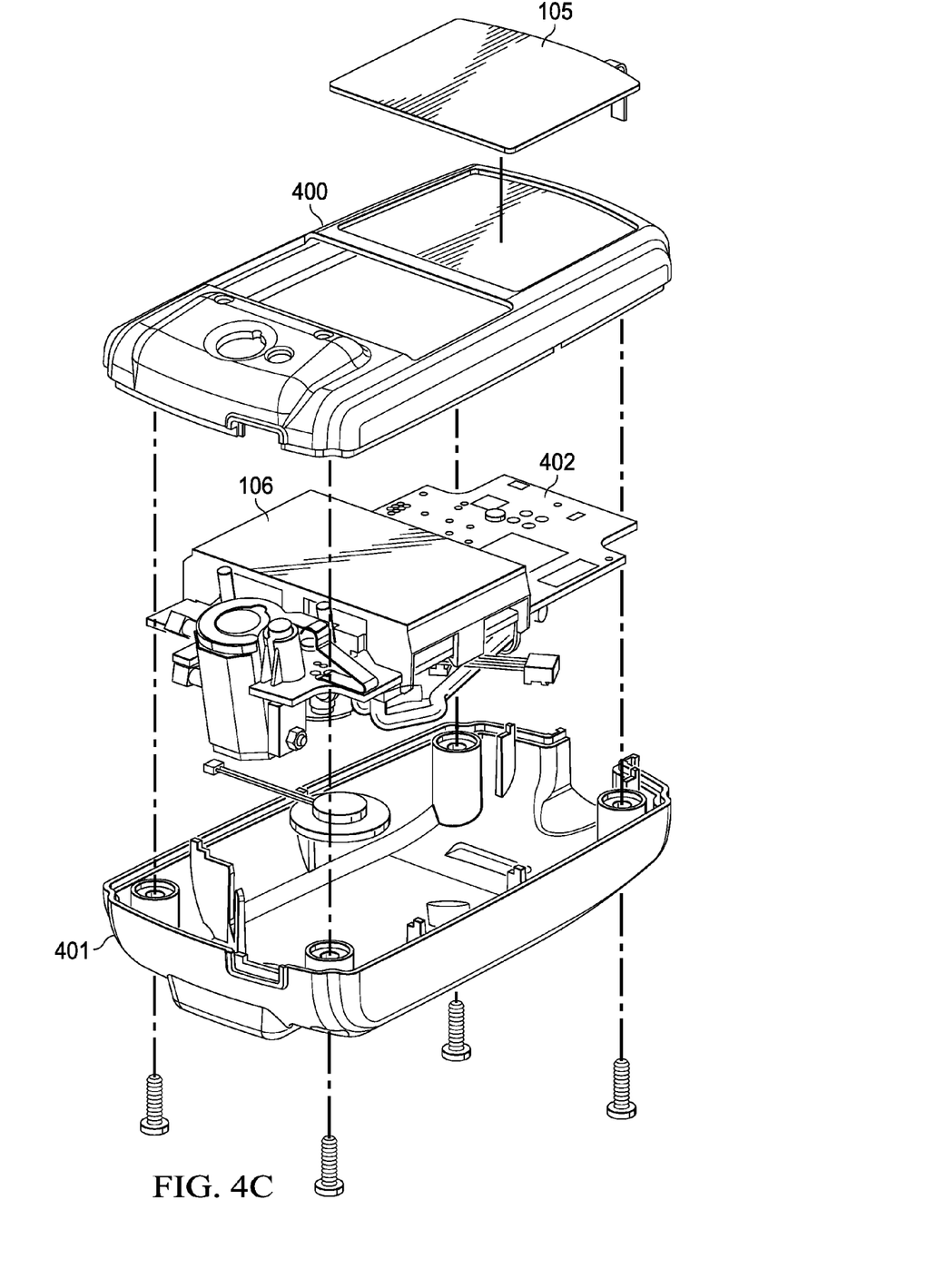
FIG. 4C is an exploded view of major structural components of the handheld unit shown in FIG. 1A.
Figure 4D:
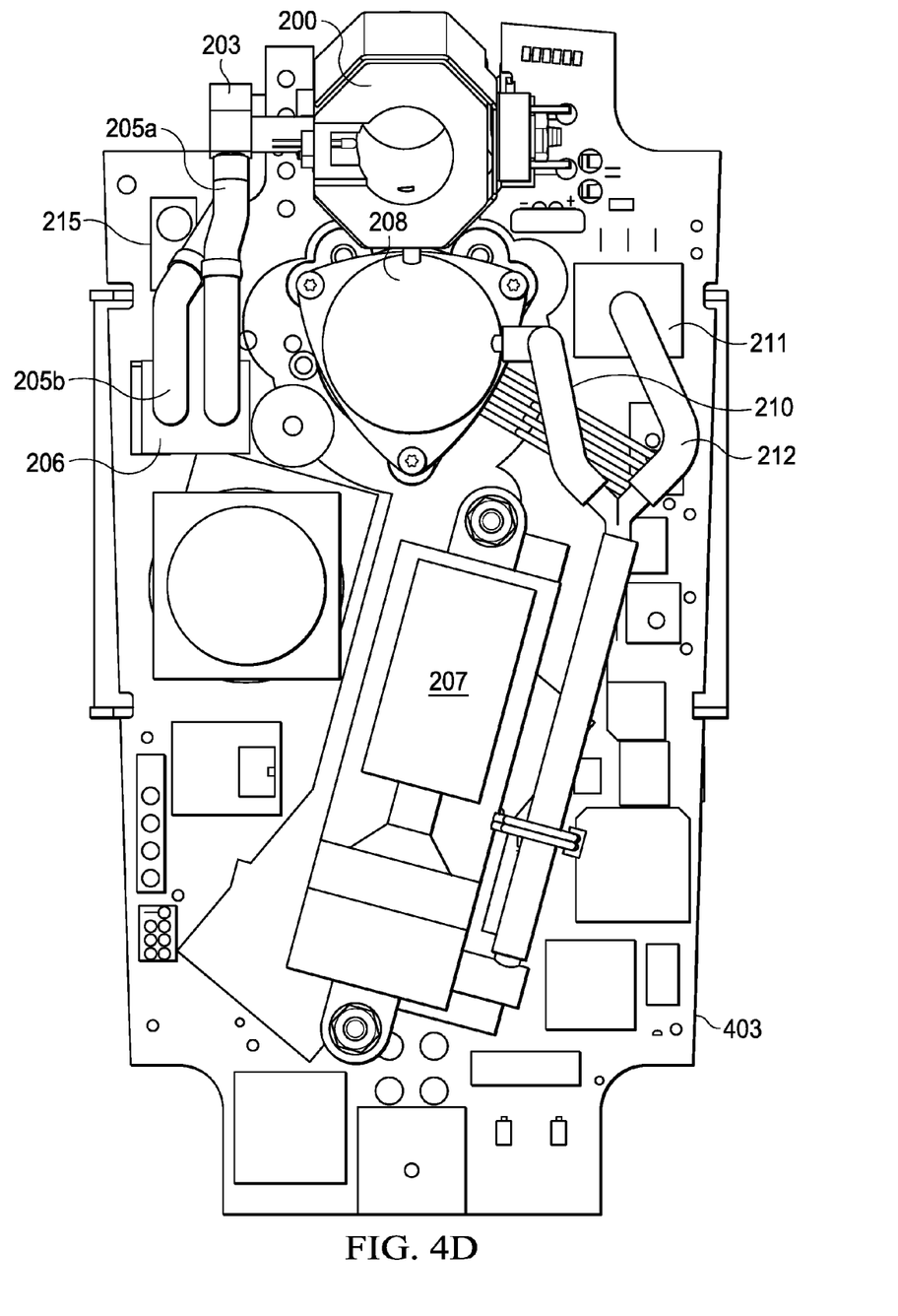
FIG. 4D is a plan view diagram showing one side of the printed circuit board of FIG. 4C, including selected subsystems shown in FIG. 2.
Figure 4E:
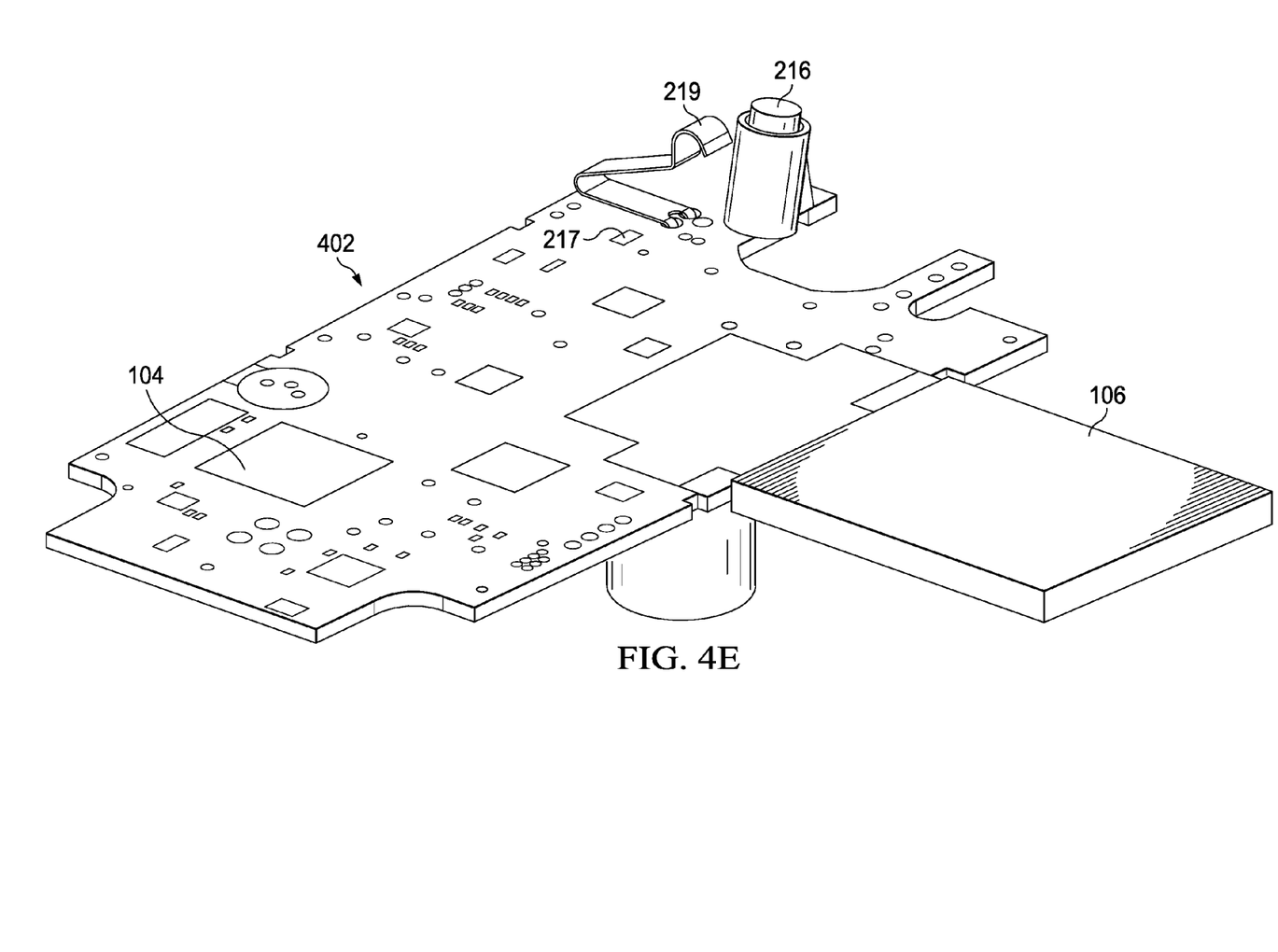
FIG. 4E is a plan view diagram showing the opposite side of the printed circuit board of FIG. 4C, including the oral IR sensor and the face proximity subsystem-to-electrode clip shown in FIG. 2.

FIG. 4C is an exploded view of handheld unit 100, including printed circuit board (PCB) 402, which supports the majority of the subsystems shown in FIG. 2. The back face of PCB 402 is shown in FIG. 4D and the front face of PCB 402 is shown in FIG. 4E. (In FIG. 4A, display 106 has been folded to the side to expose the front surface of PCB 402). As discussed above, PCB 402 is preferably conformal coated to protect face proximity sensor 217 from humidity and condensation.

FIG. 4E particularly shows spring contact 219, which contacts electrode 218, as shown in FIG. 4B, to provide the electrical connection to face proximity sensor 217. FIG. 4E also shows oral IR sensor 216, which extends through a corresponding aperture in front panel 400 of FIG. 4A to allow and IR beam sensing of the back of the user's throat.

Figure 5:
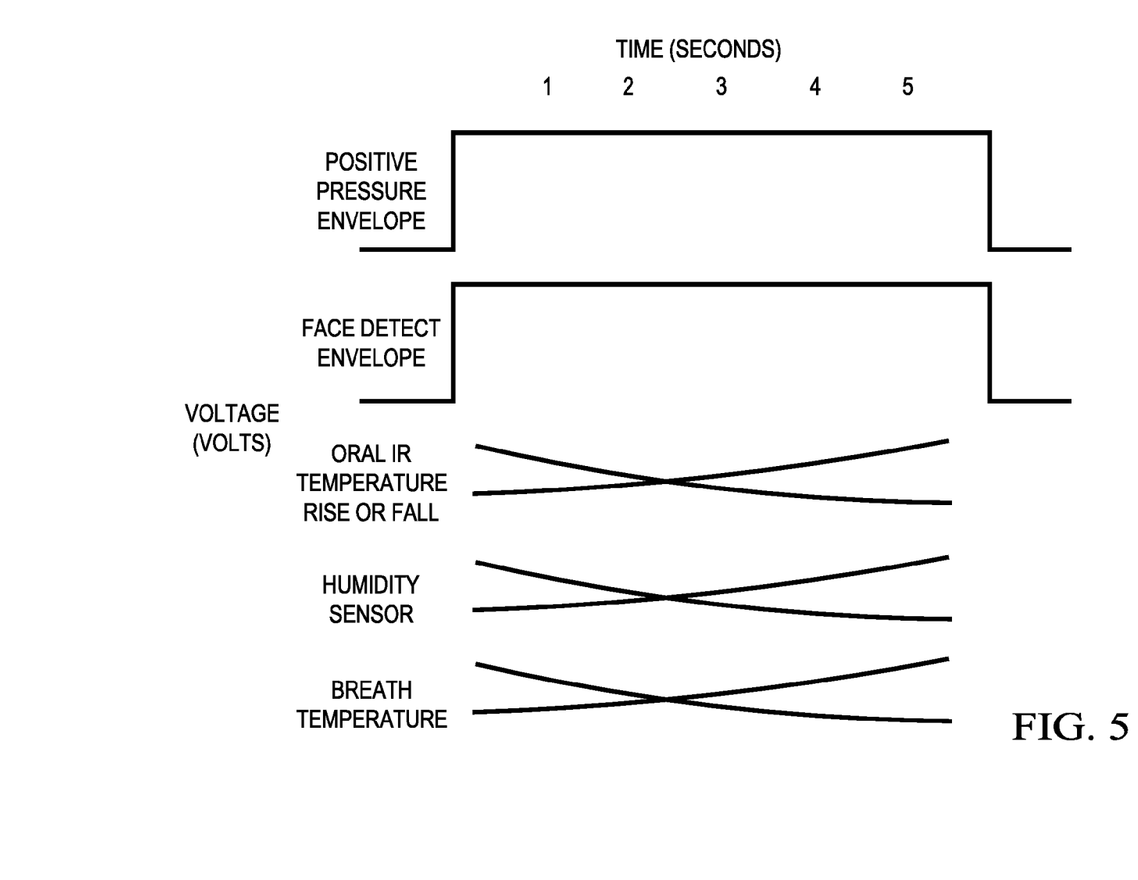
FIG. 5 is a conceptual timing diagram illustrating an anti-circumvention method using multiple sensors according to one representative embodiment of the principles of the present invention.

According to the principles of the present invention, the set of sensors, including breath temperature sensor 204, differential pressure sensor 206, humidity sensor 215, oral IR sensor 216, and face proximity sensor 217 can be used in various combinations, depending on such factors as environmental conditions, to ensure that a human subject is providing air to handheld unit 100 (i.e., the breath sample is not being provided by a mechanical source, such as an air compressor, air canister, or balloon). FIG. 5 provides an exemplary graphical representation of the sensor outputs over time and when they would be valid during the breath test.

As shown in FIG. 5, a detection envelope is established by the output of at least one of differential pressure sensor 206 and face proximity sensor 217. At least one of humidity sensor 215, oral IR sensor 216, and breath temperature sensor 204 is then used during the detection envelope to detect transitional changes from ambient conditions. Depending on the ambient conditions, these transitional changes can be either positive going or negative going, as shown in FIG. 5. (In some cases, the response curve of the given humidity sensor 215, oral IR sensor 216, or breath temperature sensor 204 may be flat, in which case interlock system processor 104 may discard the sensor output).

In other words, during a valid test, pressure sensor 206 should show minimal change at its output and face proximity sensor 217 should provide a constant active output signal, which in the preferred embodiment, is a logic 1. At least one of the set of transitional sensors (humidity sensor 215, oral IR sensor 216, and breath temperature sensor 204) should show a change in output voltage during the detection envelope defined by pressure sensor 206 and/or face detector 217.

Generally, the more sensors that can be used the more difficult the system becomes to defeat. However, as discussed above, under certain environmental conditions, humidity sensor 215, oral IR sensor 216, and breath temperature sensor 204 may not detect a change relative to ambient (i.e., the sensor output response is flat during the test because any change created by human proximity to the sensor results in little, if any change, in the sensed parameter relative to ambient.) In addition, one or more of the set of sensors could fail. In the case of a flat sensor response curve or a sensor failure, interlock system controller 104 preferably discards the output of that sensor in determining the validity of the test. If too many sensors fail to provide valid information for interlock system controller 104 to validate the test, a conventional validation function, such as a blow-hum test, can be initiated.

Table I provides exemplary test validation procedures in pseudo-code according to the principles of the present invention. These procedures are preferably executed by interlock system processor 104 in response to firmware and the sensor outputs. In the procedure shown in the left column, the detection envelope is established using both differential pressure sensor 206 and face proximity sensor 217 and the test is validated using a change in ambient detected by one of humidity sensor 215, oral IR sensor 216, and breath temperature sensor 204. The procedure shown in the middle column is similar, with the exception that the test is validated when a change is detected in at least two of the oral temperature, humidity, and breath temperature parameters from ambient. The third column shows an exemplary procedure for determining whether the output from a given humidity sensor 215, oral IR sensor 216, or breath temperature sensor 204 is a valid and suitable for use for breath test validation. Various other combinations of sensor outputs can also be used according to the inventive principles.

TABLE 1

| Multi-sensor Scheme - Simple (Blow-hum as fall back) | Multi-sensor scheme requiring at least 2 sensors (Blow-hum as fall back) | Valid sensor check |
|---|---|---|
| While air pressure = positive.<br>{<br>  While face sensor = positive<br>  {<br>  If Oral IR = delta<br>  If humidity sensor = delta<br>  If breath temperature = delta<br>  Then Breath sample = valid<br>  }<br>}<br>Display results<br>Else<br>Abort test<br>(or Else<br>Display "abort test - use blow hum"<br>Force blow hum technique) | While air pressure = positive.<br>{<br>  While face sensor = positive<br>  {<br>  If Oral IR = delta<br>  ++acv<br>  If humidity sensor = delta<br>  ++acv<br>  If breath temperature = delta<br>  ++acv<br>  Then Breath sample = valid<br>  ++acv<br>  }<br>}<br>If acv >= 2<br>Display results<br>Else<br>Abort test<br>(or Else<br>Display "abort test - use blow hum"<br>Force blow hum technique) | Delta = record start value<br>Record stop value<br>If not equal<br>And (or)<br>Delta >= x<br>Sensor works and can be used.<br>rise or fall in start value |

In sum, the principles of the present invention provide circuits, systems, and methods for validating tests taken by a sobriety testing device or system. Advantageously, the difficulties associated with the conventional breath manipulation validation procedures, such as the blow-hum, blow-suck, and blow-blow techniques, are reduced or eliminated. (Although these techniques are still available for use, if necessary, as a backup.) While demonstrated in conjunction with a vehicle interlock system based on breath testing for alcohol with a fuel cell, these principles are equally applicable to other types of devices and systems that test for intoxication, including stand alone intoxication testers and devices for testing for other forms of controlled substances.

Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed might be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

What is claimed is:

1. A system for testing for intoxication of a human comprising:
   a first subsystem for testing for a substance in the breath of a human;
   a second subsystem for validating the results of an intoxication test performed with the first subsystem, comprising:
     at least one first sensor activated in response to a change in capacitance caused by the presence of an inherent capacitance of the human for generating a first signal defining a time envelope; and
     at least one second sensor for generating a second signal in response to a change from an ambient condition caused by the presence of the human, the at least one second sensor comprising an infrared temperature sensor for reflecting an infrared beam off the back of the throat of the human; and
   a third subsystem for validating the results of the intoxication test in response to the first and second signals.

2. The system of claim 1, wherein the first subsystem comprises a fuel cell for detecting alcohol.

3. The system of claim 1, wherein the at least one second sensor further comprises a humidity sensor.

4. The system of claim 1, wherein the at least one second sensor further comprises a breath temperature sensor.

5. The system of claim 1, wherein the system for testing for intoxication forms a part of a vehicle interlock system.

6. A method for preventing circumvention of a intoxication test comprising:
   performing an intoxication test;
   defining a detection time envelope with a capacitive sensor measuring a change in capacitance caused by an inherent capacitance of a human test subject proximate the capacitive sensor;
   sensing with at least one second sensor for a change from an ambient condition caused by the presence of the human test subject proximate the second sensor, the second sensor comprising an infrared temperature sensor for reflecting an infrared beam off the back of the throat of the human test subject; and
   validating the intoxication test when a change from the ambient condition is detected by the second sensor during the time envelope defined by the capacitive sensor.

7. The method of claim 6, wherein the at least one second sensor further comprises a breath temperature sensor.

8. The method of claim 6, wherein the at least one second sensor further comprises a humidity sensor.

9. The method of claim 6, further comprising:
   sensing with a third sensor for a change from another ambient condition caused by the presence of the human test subject proximate the third sensor; and validating the intoxication test when a change from the ambient condition is detected by the second sensor and a change from the another ambient condition is detected by the third sensor during the time envelope defined by the capacitive sensor.

10. The method of claim 6, wherein defining a detection time envelope comprises defining a detection time envelope with a plurality of sensors, including the capacitive sensor, activated in response to the presence of a human test subject.

11. A system for testing for intoxication of a human comprising:
- a first subsystem for testing for a substance in the breath of a human; and
- a second subsystem for validating the results of an intoxication test performed with the first subsystem, comprising:
  - at least one first sensor for detecting the presence of the human and defining a detection time envelope; and
  - at least one second sensor for validating the results of the intoxication test during the detection time envelope, comprising an infrared temperature sensor for reflecting an infrared beam off the back of the throat of the human.

12. The system of claim 11, wherein the at least one first sensor comprises a capacitive facial proximity sensor activated in response to a change in capacitance caused by the presence of an inherent capacitance of the human.

13. The system of claim 11, wherein the at least one first sensor comprises a differential air pressure sensor activated in response to air pressure generated by the breath of the human.

14. The system of claim 11, wherein the at least one first sensor comprises:
- a capacitive facial proximity sensor activated in response to a change in capacitance caused by the presence of an inherent capacitance of the human; and
- a differential air pressure sensor activated in response to air pressure generated by the breath of the human.

15. The system of claim 11, wherein the at least one second sensor comprises a breath temperature sensor.

16. The system of claim 11, wherein the at least one second sensor comprises a humidity sensor.

* * * * *